(12) United States Patent
Hill

(10) Patent No.: US 7,760,350 B2
(45) Date of Patent: Jul. 20, 2010

(54) GLAZING INSPECTION

(75) Inventor: Barry Raymond Hill, St Helens (GB)

(73) Assignee: Pilkington Group Limited, St. Helens, Merseyside (GB)

( * ) Notice: Subject to any disclaimer, the term of this patent is extended or adjusted under 35 U.S.C. 154(b) by 49 days.

(21) Appl. No.: 12/295,134

(22) PCT Filed: Mar. 28, 2007

(86) PCT No.: PCT/GB2007/050165
§ 371 (c)(1),
(2), (4) Date: Nov. 20, 2008

(87) PCT Pub. No.: WO2007/110672
PCT Pub. Date: Oct. 4, 2007

(65) Prior Publication Data
US 2009/0185179 A1    Jul. 23, 2009

(30) Foreign Application Priority Data
Mar. 29, 2006  (GB) ................................. 0606217.8

(51) Int. Cl.
*G01N 21/00* (2006.01)
(52) U.S. Cl. ................................. 356/239.1; 356/237.2
(58) Field of Classification Search .............. 356/239.1, 356/237.2, 600
See application file for complete search history.

(56) References Cited

U.S. PATENT DOCUMENTS

| | | | |
|---|---|---|---|
| 4,341,469 A * | 7/1982 | Gardiner et al. | 356/239.1 |
| 4,492,477 A | 1/1985 | Leser | |
| 4,645,337 A * | 2/1987 | Obenreder | 356/128 |
| 5,134,278 A | 7/1992 | Nelen | |
| 2003/0151739 A1 | 8/2003 | Capaldo et al. | |
| 2005/0259245 A1 | 11/2005 | Cemic et al. | |

FOREIGN PATENT DOCUMENTS

| | | |
|---|---|---|
| EP | 0 930 498 A2 | 7/1999 |
| JP | 8-327561 A | 12/1996 |
| WO | WO 00/26647 A1 | 5/2000 |
| WO | WO 01/49043 A1 | 7/2001 |
| WO | WO 2004/088294 A1 | 10/2004 |
| WO | WO 2006/012551 A1 | 2/2006 |
| WO | WO 2006/029536 A1 | 3/2006 |

OTHER PUBLICATIONS

Search Report under Section 17(5) issued in priority application No. GB0606217.8, Jul. 10, 2006, The Patent Office, South Wales, UK.
Search Report under Section 17(6) issued in priority application No. GB0606217.8, Sep. 1, 2006, The Patent Office, South Wales, UK.
* Forms PCT/ISA/210 (International Search Report) dated Jul. 30, 2007.

* cited by examiner

*Primary Examiner*—Roy Punnoose
(74) *Attorney, Agent, or Firm*—Buchanan Ingersoll & Rooney PC

(57) ABSTRACT

A method of inspecting a glazing for faults involves illuminating the glazing with light having a first wavelength to produce a bright-field image, and illuminating the glazing with light having a second wavelength to produce a dark-field image. The bright-field image and dark-field image are captured using a single image capture device. The bright-field and dark-field images may be focussed onto the image capture device by a common lens. In addition, a shadowgraph image may be recorded simultaneously. The inspection method provides an improved fault detection system for glazings, such as automotive glazings.

14 Claims, 3 Drawing Sheets

GLAZING INSPECTION

BACKGROUND OF THE INVENTION

The present invention relates to the inspection of glazings, in particular, to the inspection glazings for both distorting and non-distorting faults.

During production, the glass used in automotive glazings is inspected for various defects that may affect the optical quality of the finished glazing product. For example, the glass may have faults acquired through processing, such as, edge faults, brillantatura and shiners from the cutting and grinding processes used to cut the glass to size. Alternatively, faults may arise through distortion, thickness and curvature variations from the firing and bending processes used to shape the glass. For example, a secondary image may be seen when viewing an object through shaped glass. This is the case for both single ply and laminated glazings.

Faults may also arise within the body of the glass, from the glass-making process, or on the surface of the glass from processing, either during or after manufacture. For example, glass made using the float process may have small gas bubbles and nickel sulphide inclusions within the body of the glass, or areas where cutlet (recycled glass) has not melted properly, and formed fused regions. The surface of the glass may have tin specks, roller imprints (from the lehr rollers), abrasions, chips and chill cracks. Whilst some of these faults can be detected between the glass leaving the float line and further processing, such as firing and bending, some, such as abrasions, cannot be detected until a final inspection, as they may arise at any point in the processing of the glass. These faults have implications on the final quality, cosmetic appearance and durability of a glazing.

Typically, faults in glass are detected using optical inspection processes. These are where the glass is illuminated either in transmission or reflection, and the variations in transmitted light used to determine whether a fault is present. One well known quality inspection method is the shadowgraph. A glazing is positioned between a localised light source (a high intensity point source) and a screen, and a shadowgraphic image of the glazing is projected onto the screen, and recorded using a CCD (charge-coupled device) camera. The shadowgraph of a glazing is characterised by illumination variations that are related to the transmitted distortion of the glazing, caused by thickness variations in the glass. These thickness variations result in an effect known as "wedge", where shallow, wedge-shaped sections of glass are seen, causing deflection of light resulting in optical distortion. Variations in the wedge angle result in light converging or diverging, giving the illumination variations of the shadowgraph. Shadowgraphs may be generated from flat or curved glazings, and may be incorporated as the final inspection step in a glass processing line.

Other optical techniques may also be used for the inspection of glass. Faults within the glass may be imaged using both bright-field and dark-field techniques. Bright-field techniques can be used to detect small faults (as little as 0.2 mm in size), both in focus, to detect non-distorting faults, and out of focus, to detect distortion. Dark-field techniques may also be used to detect small faults (as little as 0.2 mm in size). However, as all faults scatter light, images of distorting faults can be viewed in focus. Distorting faults may also be viewed using shadowgraph techniques.

Separate bright-field and dark-field measurements are needed to build up an accurate picture of the quality of a glazing. The images generated by each technique may be recorded using separate detectors and integrated in a processing step. Alternatively, both bright-field and dark-field image components of a single image may be combined onto a single detector. However, when this is done, the combination of a peak in the dark-field signal with a trough in a bright-field signal may result in a low combined response, as many faults which scatter light to produce a dark-field image will absorb light in a bright-field image. In addition, the dynamic range of the signals measured is compromised, and information is lost. Determining whether a fault is present or meets pass/fail criteria, is therefore complex, and false rejects may occur. Such methods are therefore difficult to implement successfully on a production line.

It is therefore desirable to find a way to integrate bright-field and dark-field imaging techniques effectively for use in an optical inspection method.

SUMMARY OF THE INVENTION

The present invention aims to address the problems of prior methods by a method of inspecting a glazing for faults, comprising illuminating the glazing, with light having a first wavelength, to produce a bright-field image; illuminating the glazing, with light having a second wavelength, to produce a dark-field image; illuminating the glazing, with light having a first wavelength, to produce a shadowgraph image; and capturing the bright-field image, the dark-field image and the shadowgraph image using a single image capture device.

By generating the bright-field and dark-field images using separate wavelength, as well as generating a shadowgraph image simultaneously, it is possible to use a single image capture device to record the images. By using a single image capture device, each image is focused onto the device in the same way, resulting in images having the same geometry, which can be combined, for example, by addition or subtraction. This results in improved detection of both distorting and non-distorting faults.

Preferably, the bright field image, the dark-field image and the shadowgraph image are focussed onto the image capture device, using a common lens.

Preferably, the bright-field image and shadowgraph image are formed with light from the same light source. Preferably, the shadowgraph image is focussed onto the image capture device by the common lens.

Preferably, the image capture device is a CCD (charge-coupled device) camera.

The light having a first wavelength is preferably produced by a point light source. The point light source may be an LED (light emitting diode). Preferably, the light having a second wavelength is produced by a line light source. The line light source may comprises a linear array of LEDs (light emitting diodes). Preferably, the glazing inspected is an automotive glazing.

The present invention also provides an apparatus for performing such a method.

BRIEF DESCRIPTION OF THE DRAWINGS

The invention will now be described by way of example only, and with reference to the accompanying drawings in which.

DETAILED DESCRIPTION OF THE INVENTION

In the present invention, it has been appreciated that light from two different wavelength sources can be used to generate bright-field and dark-field images of faults in a glazing, and be detected using a single image capture device. By successfully combining bright-field and dark-field techniques, it is also possible to generate a shadowgraph image of the glazing using the same source of light as for the bright-field image.

Figure 1:
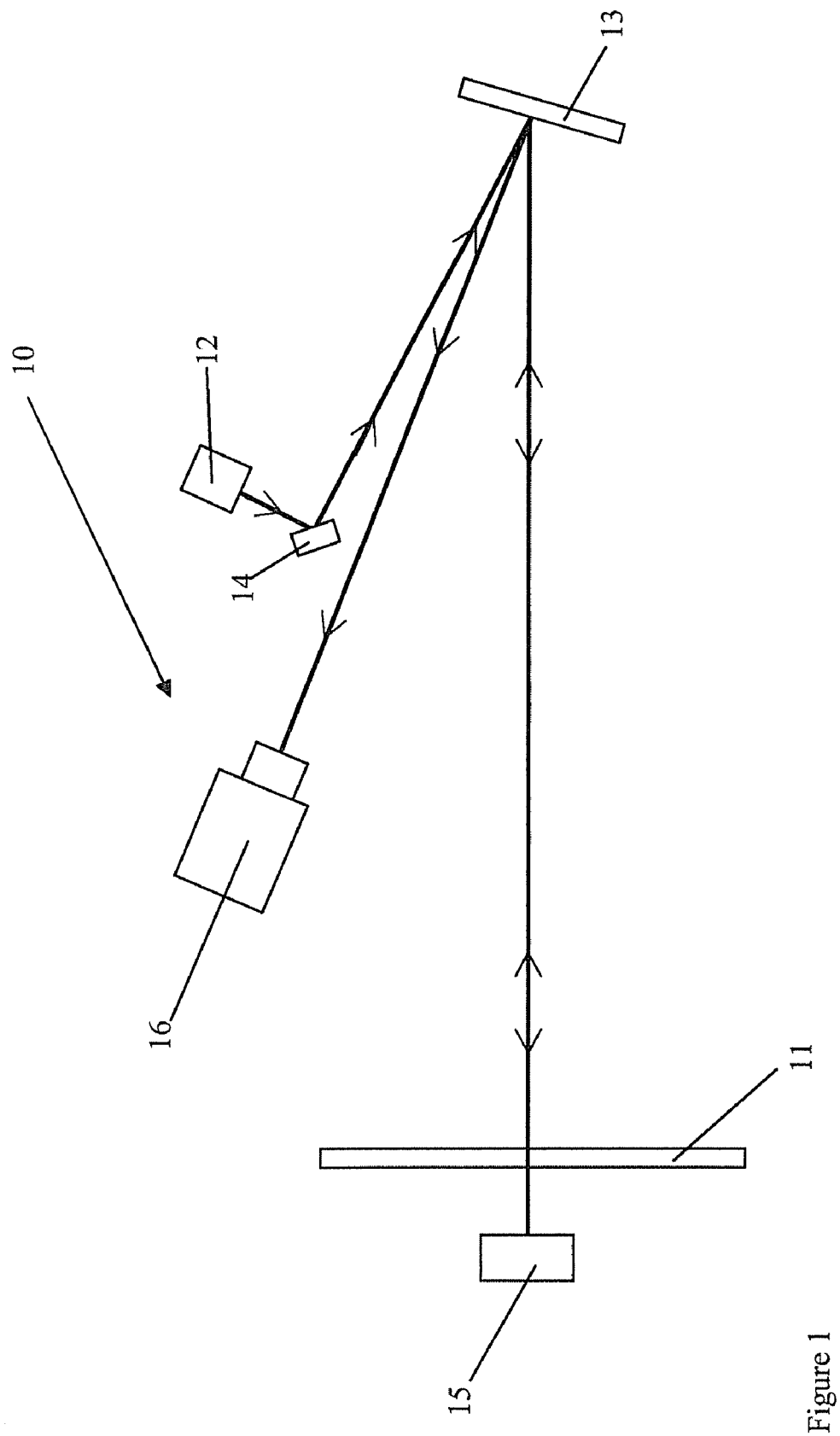
FIG. 1 is a schematic ray diagram of an optical inspection apparatus set up for bright-field imaging.

FIG. 1 shows a schematic representation of optical inspection apparatus set up for bright-field imaging. The optical inspection apparatus 10 is shown with a glazing 11 (supported on a stand, which is not shown) in position to be inspected in transmission. The apparatus 10 comprises a LED (light emitting diode) point light source 12, which emits light reflected by a large mirror 13 and incident onto the glazing 11. The light from the LED point light source 12 is directed to the large mirror by a small mirror 14. A strip spherical surface mirror 15 is positioned directly behind the glazing 11, and reflects light back through the glazing to the large mirror 13. This light is then reflected by the large mirror 13, back past the edge of the small mirror 14, to an image capture device 16. The image capture device 16 records in focus images of non-distorting defects and out of focus images of distorting defects. The image capture device 16 is also able to detect illumination variations caused by any wedge effect within the glazing, allowing a shadowgraph image to be recorded simultaneously. The shadowgraph image is an out of focus image of any distorting defects present in the glazing. Light travels from the glazing 11 to the strip spherical surface mirror 13 and back again, such that the defect appears to be behind the mirror and therefore out of focus. Alternatively, a beam splitter may be used in place of the small mirror 14, in which case the apparatus is set up such that light reflected by the large mirror 13 into the image capture device 16 also passes through the beam splitter.

In FIG. 1, the angle between the light travelling from the small mirror 14 to the large mirror 13, and the light returning from the large mirror 13 to the image capture device 16 has been exaggerated for clarity. In practice, the angle is minimised to ensure that the light travelling to and being reflected from the spherical surface mirror 14 travels the same path, so that only one image of each defect is detected. If desired, it is possible to remove the large mirror 13, and have both the light source 12 and the image capture device 16 pointing directly at the glazing 11. In this situation, the strip spherical surface mirror 15 is replaced with a full spherical surface mirror.

Figure 2:
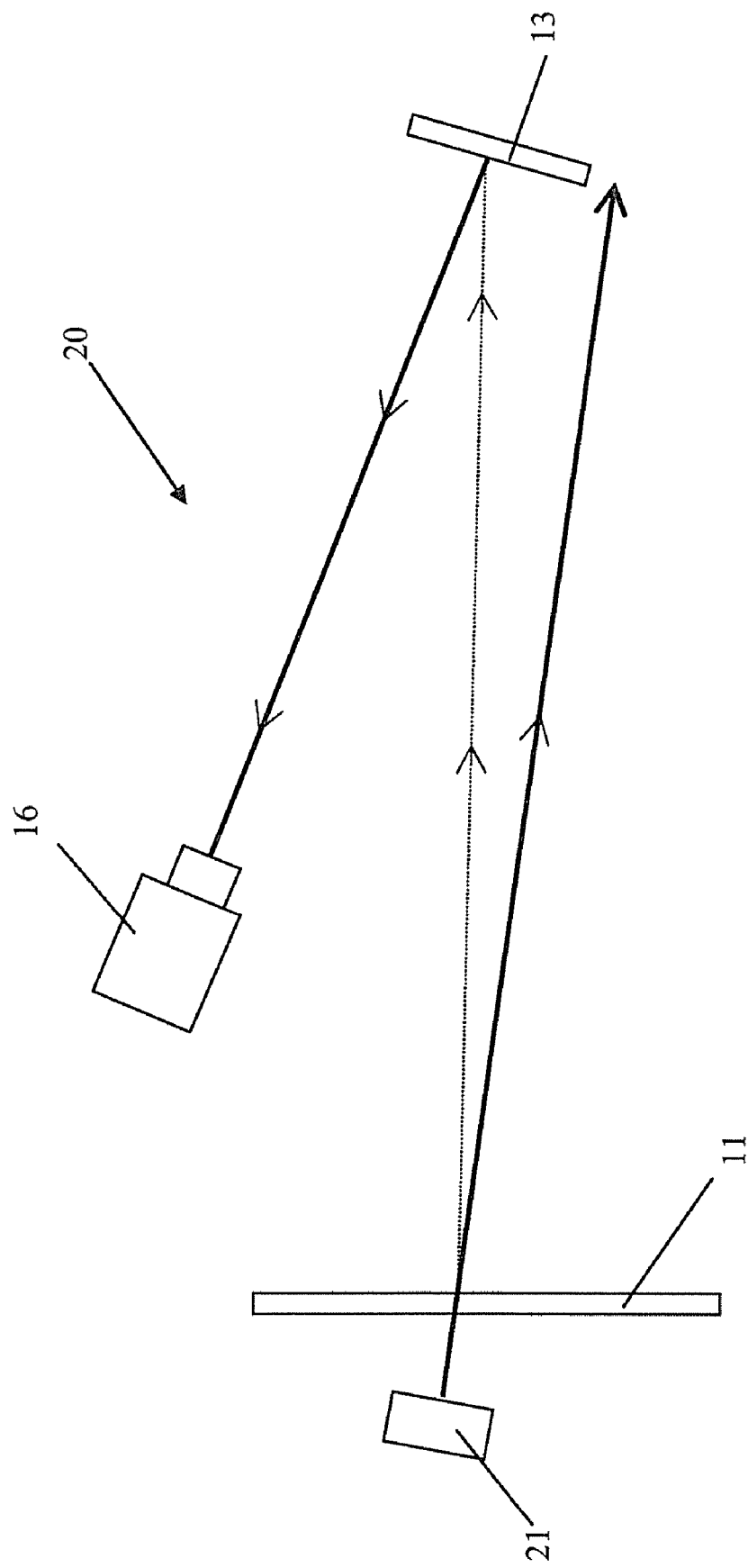
FIG. 2 is a schematic ray diagram of an optical inspection apparatus set up for dark-field imaging.

FIG. 2 shows a schematic representation of optical inspection apparatus set up for dark-field imaging. The optical inspection apparatus 20 is shown with a glazing 11 (supported on a stand, which is not shown) in position to be inspected in transmission. The apparatus 20 comprises an LED (light emitting diode) line light source 21, arranged vertically behind the glazing 11, which comprises a linear array of LEDs, and is approximately 1 m in length. The line light source 21 is arranged such that the light transmitted directly through the glazing passes the side of the large mirror 13, such that only light scattered by defects and faults within the glazing 11 is reflected by the large mirror 13 to an image capture device 16. The image capture device 16 records all faults in focus, as all faults, including distorting faults, scatter light.

Figure 3:
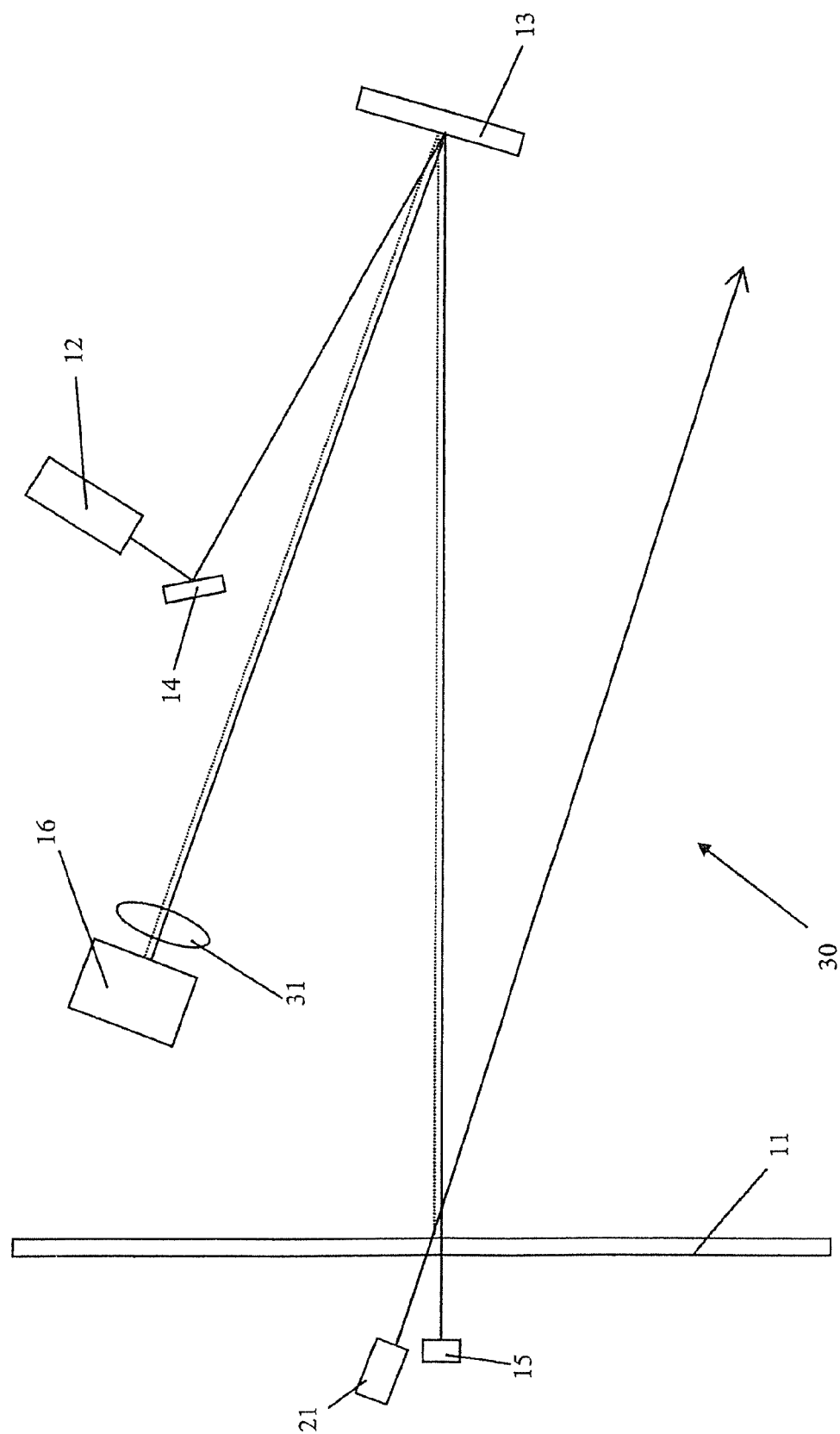
FIG. 3 is a schematic ray diagram of the optical inspection system for performing the method of the present invention.

FIG. 3 is a plan view of the set up of the optical inspection system for performing the method of the present invention. The bright-field imaging apparatus shown in FIG. 1 and the dark-field imaging apparatus shown in FIG. 2 have been combined into a single optical inspection system. The system 30 allows the glazing 11 to be inspected in transmission, and bright-field and dark-field images to be recorded on a single image capture device. Shadowgraph images generated by the LED point light source 12 may also be recorded. Distorting faults appear highlighted in the shadowgraph image by a bright region or "halo".

In order to combine bright-field and dark-field imaging, the two light sources operate at different wavelengths. Preferably, the LED point light source 12 used for bright-field imaging emits green light, and the LED line light source 21 used for dark-field imaging emits red light. However, alternative light sources may be used, such as a laser, for both the point light source and line light source. As with the apparatus in FIG. 1, the small mirror 14 may be replaced with a beam splitter, and the apparatus set up such that light reflected towards the image capture device 16 passes through the bean splitter (light from the LED point source and forming the bright-field image is shown as a solid line in FIG. 3).

The LED line light source 21 is set up to illuminate the glazing very close to the point where the LED point light source 12 illuminates the glazing in focus (light from the LED line source and forming a dark-field image is shown in FIG. 3 as a dotted line, slightly displaced from the line representing the bright-field image for clarity). Light from the LED point light source 12, which is reflected or transmitted directly by faults in the glazing, is reflected from the large mirror 13 to the image capture device 16, forming a bright-field image. Illumination variations in the light reflected back to the camera from the LED point light source 12 are used to form a shadowgraph image. Light from the LED line light source 21 is scattered by faults in the glazing, and then reflected to the image capture device 16 by the large mirror 13, forming a dark-field image. Light from the line light source 21 transmitted directly though the glazing 11 misses the large mirror 12 and forms no part of the image captured. Both the bright-field image and dark-field image are focussed onto the image capture device 16 by a single lens 31, common to both imaging techniques. The bright-field images and the dark-field images are therefore combined at the image capture device 16, for example, by addition or subtraction. If a shadowgraph image is generated, this will also be focussed onto the camera using the lens 31, and so will be combined with the bright-field and dark-field images.

In FIG. 3, as in FIG. 1, the angle between the light travelling from the small mirror 14 to the large mirror 13, and the light returning from the large mirror 13 to the image capture device 16 has been exaggerated for clarity, and would be minimised in practice. As with the bright-field apparatus in FIG. 1, if desired, it is possible to remove the large mirror 13, and have both the light source 12 and the image capture device 16 pointing directly at the glazing 11. In this situation, the strip spherical surface mirror 15 is replaced with a full spherical surface mirror.

Preferably, the image capture device 16 used is a L304kc series Line Scan tri-linear colour CCD camera, available from Basler AG, An der Strusbek 60-62, D-22926, Ahrensburg, Germany. The camera employs a tri-linear sensor having three lines of 4080 photosensitive elements, one covered with a red filter, one with a green filter and one with a blue filter to provide spectral separation. The camera may run in free-run mode, and has an external trigger for exposure time control. Additional lenses, such as the lens 31 shown in FIG. 3, may be used to focus the images generated onto the camera. An areascan camera may be used as an alternative image capture device, in which case the strip spherical surface mirror 15 is replaced with a full spherical surface mirror.

Each of the lines of photosensitive elements is separated by a distance of 90 μm. It is possible to use this separation to help separate the illumination by the two light sources at the glazing. A 30× magnification lens is used to focus the images of the glazing onto the camera. This produces an image separation of approximately 2.7 mm at the glazing. By separating the images, the angle at which the LED line light source 21 is positioned relative to the glazing is reduced, increasing the height range of the glazing being inspected over which the LED line light source 21 can be used without repositioning. When a blue LED is used in the LED point light source 12, the separation between the blue and red photosensitive elements is 180 μm, and so the image separation at the glazing is increased to approximately 5.4 mm.

Both the wavelength used to generate the bright-field image ($\lambda_1$) and that used to generate the dark-field image ($\lambda_2$) should be within the spectral range of the image capture device used. Preferably, the LED point light source is an LED light source available from Lumileds Lighting, LLC, 370 West Trimble Road, San Jose, Calif., 95131 USA. Preferably, the LED line source is a COBRA™ Linescan source, available, from StockerYale (IRL), Ltd, 4500 Airport Business Parl, Kinsale Road, Cork, Ireland. In the example above, the wavelength used for the line light source (red light) is 630 nm and that of the point light source (green light) 540 nm. At these wavelengths, images from the unused colour filters of the L304kc camera are generally suppressed. However, it would be possible to use different wavelength light sources, and/or an image capture device with a different spectral range to generate the bright-field and dark-field images. For example, lasers or white light sources with suitable filters may be used.

Once the images have been captured they may be displayed to an operator via a screen, or processed further by image-processing software, either immediately, or at a later date, after being stored in a memory storage device. A fault may be shown as a dark area in the bright-field image or as a bright area in the dark-field image. For faults causing distortion, where a shadowgraph image has also been generated and captured, the fault is normally seen in the bright-field image, surround by a bright region, or halo. The apparatus allows faults as small as 100 μm across to be detected.

When a linescan camera is used to capture the bright-field, dark-field and shadowgraph images, the glazing is moved through the focal point of the camera and light sources such that the entire glazing is scanned. This is typically done using a conveyor belt system. Alternatively, where an areascan camera is used to capture the bright-field, dark-field and shadowgraph images, the glazing remains stationary whilst the images are captured. Such a camera is useful for off-line image capture.

With suitable automation, images may be captured from glazings moving on a processing or production line. The method of the present invention may be used to inspect single ply or laminated glazings, each of which may be flat or curved. Preferably, the glazings inspected are automotive glazings, for example, sidelights, backlights or windscreens. Alternatively, the glazings inspected may be for architectural use. Preferably, the method of the present invention is used as a final inspection on a glass processing line.

The invention claimed is:

1. A method of inspecting a glazing for faults, comprising: illuminating the glazing, with light having a first wavelength, to produce a bright-field image; illuminating the glazing, with light having a second wavelength, to produce a dark-field image; illuminating the glazing, with light having a first wavelength, to produce a shadowgraph image; and capturing the bright-field image, the dark-field image and the shadowgraph image using a single image capture device.

2. The method of claim 1, further comprising focusing the bright field image, the dark-field image and the shadowgraph image onto the image capture device, using a common lens.

3. The method of claim 2, wherein the bright-field image and shadowgraph image are formed with light from the same light source.

4. The method of claim 2, wherein the image capture device is a CCD (charge-coupled device) camera.

5. The method of claim 2, wherein the light having a first wavelength is produced by a point light source.

6. The method of claim 2, wherein the light having a second wavelength is produced by a line light source.

7. The method of claim 1, wherein the bright-field image and shadowgraph image are formed with light from the same light source.

8. The method of claim 1, wherein the image capture device is a CCD (charge-coupled device) camera.

9. The method of claim 1, wherein the light having a first wavelength is produced by a point light source.

10. The method of claim 9, wherein the point light source is an LED (light emitting diode).

11. The method of claim 1, wherein the light having a second wavelength is produced by a line light source.

12. The method of claim 11, wherein the line light source comprises a linear array of LEDs (light emitting diodes).

13. The method of claim 1, wherein the glazing is an automotive glazing.

14. Apparatus for performing the method of claim 1.

* * * * *